United States Patent
Jussel

(10) Patent No.: US 10,398,536 B2
(45) Date of Patent: Sep. 3, 2019

(54) METHOD FOR PROCESSING A DENTAL MATERIAL, REGULATING DEVICE FOR A DENTAL FURNACE, AND DENTAL FURNACE

(71) Applicant: Ivoclar Vivadent AG, Schaan (LI)

(72) Inventor: Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 164 days.

(21) Appl. No.: 14/903,180

(22) PCT Filed: Dec. 18, 2014

(86) PCT No.: PCT/EP2014/078438
§ 371 (c)(1),
(2) Date: Jan. 6, 2016

(87) PCT Pub. No.: WO2015/091779
PCT Pub. Date: Jun. 25, 2015

(65) Prior Publication Data
US 2016/0184062 A1    Jun. 30, 2016

(30) Foreign Application Priority Data
Dec. 20, 2013 (EP) .................................... 13199130

(51) Int. Cl.
*A61C 13/08* (2006.01)
*A61C 13/20* (2006.01)
*F27B 17/02* (2006.01)

(52) U.S. Cl.
CPC ............ *A61C 13/081* (2013.01); *A61C 13/20* (2013.01); *A61C 13/206* (2013.01); *F27B 17/025* (2013.01)

(58) Field of Classification Search
CPC ..... A61C 13/081; A61C 13/20; A61C 13/206; F27B 17/025

(Continued)

(56) References Cited

U.S. PATENT DOCUMENTS 5,795,151 A      8/1998  Nonami et al.
6,303,059 B1 *  10/2001  Foser ..................... A61C 13/20
                                                              264/16

(Continued)

FOREIGN PATENT DOCUMENTS

| CA | 2034893 A1 | 7/1991 |
|---|---|---|
| RU | 2089130 C1 | 9/1997 |
| SU | 996092 A1 | 2/1983 |

*Primary Examiner* — Erin Snelting
(74) *Attorney, Agent, or Firm* — Ann M. Knab; Thad McMurray

(57) ABSTRACT

The invention relates to a method for processing a dental material (28), in particular pressing and curing a dental material, by means of —a molding insert (30) that has a pre-pressing area (22) which adjoins a molding area (14, 16), wherein the pre-pressing area (22) is designed to receive the dental material (28), and —a pressing furnace with a firing chamber (10) for receiving the molding insert (30). The method has the following steps: —introducing the dental material (28) into the pre-pressing chamber (22); —heating the firing chamber (10), in which the molding insert (30) is located, to a first temperature; —pressing the dental material (28) into the molding area (14, 16) using a pressing punch (26) by applying a force onto the pressing punch (26) during a first processing phase, wherein the pressing punch (26) is moved, and the pressing punch speed is detected as a speed profile dependent on the time; and —adjusting the firing chamber (10), in particular cooling the firing chamber to a second temperature, during a second processing phase starting at a point in time at which the detected speed profile matches a first speed profile without reducing the force applied to the pressing punch (26).

10 Claims, 2 Drawing Sheets

Figure 1:
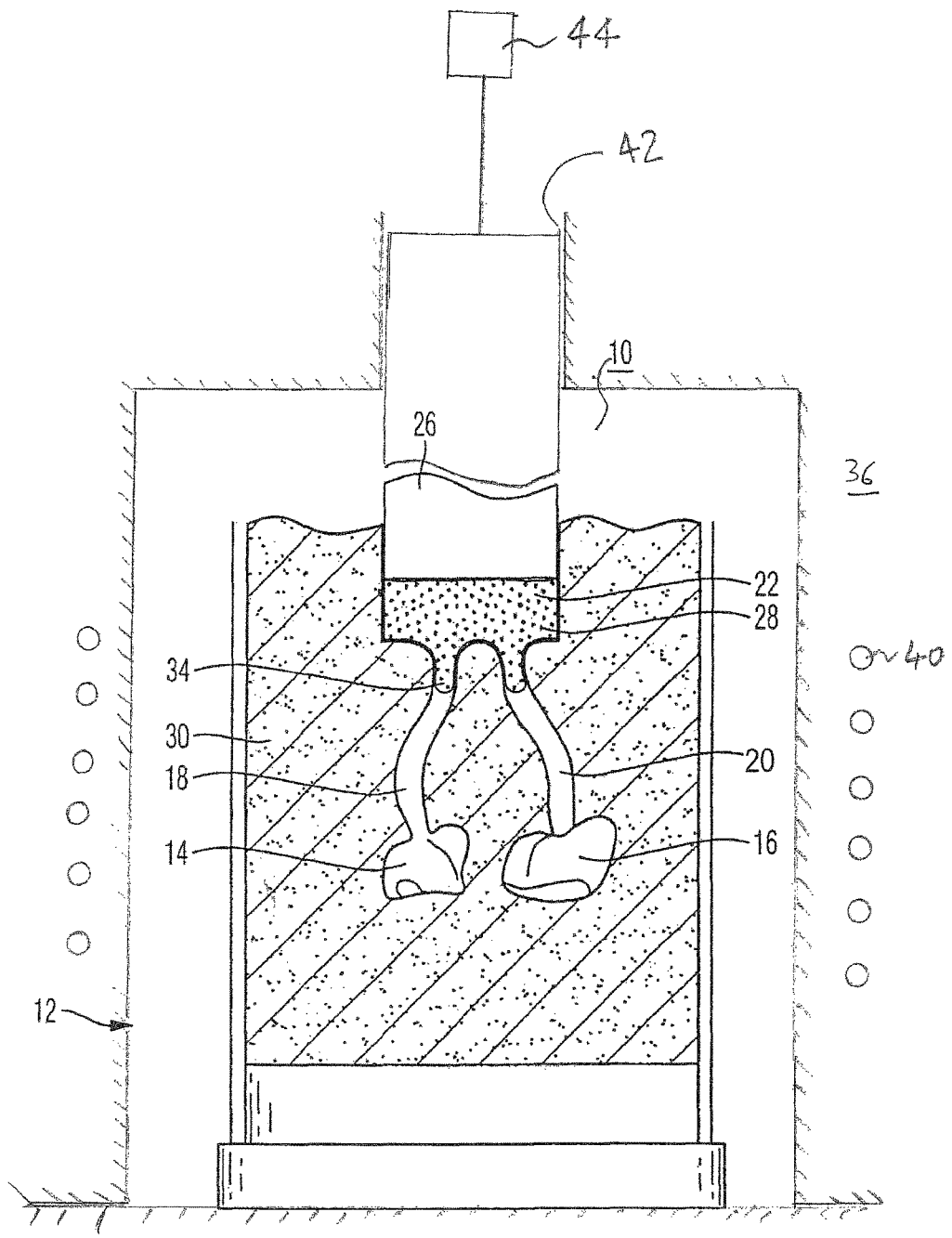

(58) Field of Classification Search
 USPC .......................................................... 264/16
 See application file for complete search history.

(56) References Cited

U.S. PATENT DOCUMENTS

| | | | |
|---|---|---|---|
| 6,306,785 B1 | 10/2001 | Nonami et al. | |
| 2004/0254667 A1* | 12/2004 | Ganley | A61C 13/0004 700/117 |
| 2005/0204796 A1* | 9/2005 | Foser | A61C 13/20 72/342.8 |
| 2008/0096148 A1* | 4/2008 | Jussel | A61C 13/20 432/32 |
| 2008/0099939 A1* | 5/2008 | Jussel | A61C 13/20 264/16 |
| 2009/0239199 A1* | 9/2009 | Cadario | A61C 13/0022 433/203.1 |
| 2013/0302459 A1* | 11/2013 | Miller | A61C 13/20 425/149 |

* cited by examiner

METHOD FOR PROCESSING A DENTAL MATERIAL, REGULATING DEVICE FOR A DENTAL FURNACE, AND DENTAL FURNACE

CROSS-REFERENCE TO RELATED APPLICATIONS

This application is a National Stage application of International Patent Application No. PCT/EP2014/078438 filed on Dec. 18, 2014, which claims priority to European Patent Application No. 13199130.9 filed on Dec. 20, 2013, the disclosures of which are incorporated herein by reference in their entirety.

The invention relates to a method for processing a dental material as well as a dental furnace comprising a regulating device according to the preamble of claim 1.

In methods of the above-mentioned type molding inserts disposed in muffles are usually used which comprise a molding area that corresponds to the desired dental object, for instance a dental restoration part. The molding area is adjoined by a pre-pressing area into which a pressing punch is inserted after the dental material which is necessary for producing the dental object has been introduced into the pre-pressing area. By heat exposure the dental material is heated, melted and pressed into the molding area by means of the pressing punch.

By means of several tests it has been determined that in spite of exactly the same heat supply conditions, the same pressing durations and the same dental materials differences were observed which can also lead to critical reductions in quality. Apparently, the different investment materials contribute to the observed deviations due to different heat capacities or masses, respectively, and thermal conduction.

In the known methods, a holding time until the pressing starts is predefined which is approximately sufficient to introduce the dental material, while also supplying heat, into the molding area in a state suitable for pressing. In this connection, it can, however, be problematic if the dental material varies with regard to its properties and parameters due to tolerances arising from the production process. In this way, the viscosity characteristics of a green product can vary from batch to batch and the position of the green product or the dental material in the furnace can also have a significant influence on the result of the methods during the production process.

Process parameters which have not been adjusted entirely to the dental material can lead to defective results, for instance to color defects or even to an incomplete pressing of the dental object wherein the latter is equivalent to a loss of the dental restoration.

Improved methods for controlling a dental firing process have become known from EP 1 915 972 B1 and DE 10 2008 012 578 B4.

In contrast, the invention is based on the task of providing a method, according to the preamble of claim 1, of an improved coordination of the process parameters when turning a dental material into a dental object, such as a denture or a partial denture, in respect of an improvement of the processing results of the dental material.

This task is solved by the independent claims. Advantageous embodiments and further embodiments may be taken from the subclaims. The features of the further embodiments can be combined with each other, if technically reasonable.

One aspect of the invention relates to a method of processing a dental material, in particular pressing a dental material. A molding insert and a pressing furnace with a firing chamber can be used for processing the dental material. The molding insert can comprise a pre-pressing area which adjoins a molding area such that the pre-pressing area and the molding area are connected to one another, preferably by means of a fluid connection. Here, a "fluid" is considered a material capable of flowing, for instance a viscous material or a solid material which has started to melt in the edge regions.

The dental material is receivable in the pre-pressing area and the molding insert or the muffle is receivable in the firing chamber of the pressing furnace.

The method may comprise the steps of:
a) introducing the dental material into the pre-pressing chamber;
b) heating the firing chamber, in which the molding insert is located, to a first temperature;
c) pressing the dental material into the molding area using a pressing punch during a first processing phase in which the pressing punch is moved and in which the pressing punch speed is detected as a speed profile dependent on the time; and
d) adjusting the firing chamber, in particular cooling the firing chamber, to a second temperature during a second processing phase starting at a point in time at which the detected speed profile matches a first speed profile.

The above-mentioned steps can be carried out subsequently in the listed order, or in a different order. The steps can also be carried out simultaneously or in such a way that they overlap one another. Thus, for instance,
steps a) and b) can be carried out simultaneously, or
steps b) and c) can overlap one another such that step c) "pressing the dental material" is started during implementation of step b) "heating of the firing chamber".

A time-dependent speed curve of the pressing punch, here referred to as pressing punch speed, can be represented two-dimensionally (2D) in a Cartesian coordinate system in which an x-axis represents time and a y-axis represents the pressing punch speed.

Instead of the time-dependent speed curve the path of the pressing punch can also be detected without further ado and be used for evaluation. The pressing punch motion can be detected in a way known per se, be it by means of a position sensor for the current position at which the pressing punch is located or with a stepping motor drive of the pressing punch by detecting the number of steps covered by the stepping motor.

A speed profile can be interpreted as a 2D profile of the pressing punch speed, wherein two profiles are considered to be matching profiles if the profiles are similar and comprise a maximum deviation below the predefined tolerance.

A speed profile can also be considered a feature of a 2D profile of the pressing punch speed, wherein the feature is defined as a request. A feature of this type can, for instance, request whether
the value of the pressing punch speed is larger or smaller compared to a threshold value, or
an increase in the pressing punch speed, which is a pressing punch acceleration, is larger or smaller compared to a threshold value.

Accordingly, two speed profiles can then be considered matching profiles if the request for a detected pressing punch speed is regarded as having been fulfilled at a certain point in time for the first time.

Alternatively, the integral can also be detected with the help of the speed profile and can be used for evaluation.

When observing speed profiles and determining the match it is also possible to take into account the point in time of the speed change, that is to say to use the overall elapsed time as a criterion, which, in respect of the evaluation, corresponds to the speed integral.

Heating or cooling the firing chamber to an end temperature in the steps b), d) can be carried out such that two parameters out of the three parameters rate of temperature change, execution time, end temperature are set, wherein the third parameter results from the set values. The desired settings can be entered or determined preferably at the pressing furnace.

In this way, a rate of temperature change for heating or cooling and a respective execution time can be set, for instance. The end temperature achieved results from the set values for the rate of temperature change and execution time.

Advantageously, the method makes it possible to reduce the cycle time. The pressing of the dental material in a first processing phase at a first furnace temperature which is higher than a second temperature which is desired and necessary for processing the dental material enables an increased heat supply into the muffle compared to general practice in which the furnace is heated to the necessary temperature from the start. In this way, the heating of the dental material in the interior of the muffle to the desired and necessary second temperature is accelerated considerably.

The furnace can be cooled, for instance, to the target temperature of the dental material, e.g. when the temperature of the dental material in the interior of the muffle has reached the desired value. The furnace chamber can be cooled by a temperature of 5% of the first temperature to the second temperature and to a maximum of 15% of the first temperature to the second temperature.

Instead, it is also possible to simply reduce the heating output in order to reduce the temperature change in the green product. A lower heating rate also reduces the temperature gradient in the muffle.

However, avoiding an excessive temperature of the dental material in the interior of the muffle by heating the firing chamber to an excessive temperature is just as important as reducing the cycle time. Overheating in the interior of the muffle over a longer period of time can lead to undesired color and/or structural changes of the dental material.

In this respect, regulating the furnace temperature based on a predefined time schedule can either lead to an incomplete result in which the dental material is not sufficiently heated as a consequence of overheating, or the regulation overshoots the target as the furnace is heated for too long at the excessive temperature such that constant overheating in the interior of the muffle damages the dental material.

However, carrying out a temperature measurement in the interior of the muffle in order to solve the above-mentioned problem would require considerable technical and financial efforts.

According to the present method the firing chamber can be cooled from a point in time at which a match of the detected speed profile with a first speed profile is determined. This renders a complex temperature measurement unnecessary, the cycle time is reduced compared to methods known up to now and the result is neither incomplete, nor does it overshoot the target. The problem is solved efficiently and with little effort only.

A further aspect of the invention relates to a regulating device for a dental furnace, in particular a pressing furnace in particular as a part of this dental furnace. The regulating device may be designed to regulate parameters of the dental furnace, including temperature, force applied to the pressing punch and parameters of the pressing punch motion, according to the method described or to one of its advantageous embodiments described below.

According to an embodiment a match with the first speed profile can be determined upon exceeding a threshold value by the pressing punch speed. A match with the first speed profile can also be determined if a pressing punch acceleration exceeds a threshold value.

According to a further embodiment the following method is used:

A press force is applied to the green product which is still hard, that is to say not capable of flowing, in this respect. The drive of the pressing punch is locked in position. Due to the elasticity of the drive and the entire system in the vertical direction the force acts continuously onto the green product, and as soon as it softens, the force is reduced while the green product simultaneously starts to move into the pressing channels.

A force sensor which can be realized by detecting the driving current of the pressing punch drive, or a path sensor can inventively detect when the green product starts to become soft and can thus determine the ideal point in time for the onset of deformation.

In this way, the ideal point in time for the start of the pressing process can be selected quasi automatically with the help of surprisingly simple means.

In these cases, a feature of the 2D profile of the pressing punch speed is considered a first speed profile, the feature being defined as a request.

A match with the first speed profile can also be determined upon reaching a maximum of the pressing punch speed, wherein preferably the first speed profile represents an impulse. In this case, the first speed profile is considered a 2D profile of the pressing punch speed, wherein a match between the detected speed profile and the stored, first speed profile is defined as a similarity of the profiles.

According to an embodiment a force in the range of 200 to 400 N and of preferably about 250 N which is particularly constant can be applied to the pressing punch in order to press the dental material into the molding area. The application of the force to the pressing punch can be started during the heating of the firing chamber comprising a built-in molding insert (see also the above-mentioned remarks on the overlapping of steps b), c) of the method). The application of the force can mark the start of the first processing phase, wherein the application of the force is continued during the second processing phase. The second processing phase can be terminated by terminating the application of force onto the pressing punch.

The second processing phase can be terminated by means of the following closure criteria:

i) if a match of the detected speed profile with a second speed profile is determined, or ii) after expiration of a period of time which corresponds to a maximum duration of the second processing phase, or iii) if the pressing punch path exceeds a threshold value.

About i):

The deviation of the pressing punch speed from a predefined profile is detected, wherein it is to be understood that as a rule different muffles exhibit different speed profiles. However, in the case of molding inserts pressing channels are always provided to which cavities adjoin which are designed to form the dental objects or dental restoration parts. When the dental material enters into the pressing channels or into the molding area the penetration rate is typically reduced as friction is relatively high thereat and increases the longer the effective friction surface is between the ceramic dental material and the channel wall. As soon as the front part of the investment material has reached the cavity, the friction does, however, not or not substantially increase further; accordingly, this corresponds to a constant penetration rate until the cavity is filled.

Even if the length of the pressing channels, which are also referred to as reception channels, and the height of the cavities vary from muffle to muffle, this basic penetration speed profile always exists which is followed by a reduction of the penetration speed in a second processing phase, wherein a compression of the dental material takes place.

Advantageously, it is determined now that if the penetration rate deviates from this basic curve, that is to say if it increases to a greater extent than in correspondence with the first speed profile, this can mean that at this point in time a further cavity is opened up, typically when the muffle bursts. This situation can be detected when a match of the detected speed profile with a second speed profile is determined, for instance when it is determined that a threshold value is exceeded by the pressing punch speed or by the pressing punch acceleration. In this situation, if an application of the force to the pressing punch is stopped, then the dental restoration part can be used, at least if the pressing process is in a relatively advanced state.

If in the course of the pressing process, the movement of the pressing punch and the associated progressive movement of the dental material no further cavity is opened up, typically as the muffle does not burst, then the pressing punch speed decreases. In fact, the speed can drop to zero, it is, however, preferred to interrupt the pressing process in advance as the pressing punch speed can have a residual value of greater than zero even if the molding area has already been filled completely by the dental material. The reason for this is that in this phase the dental material cannot advance any further but that it is, however, compressed by the pressing pressure and possibly penetrates the muffle at a microscopic scale, or the muffle stretches a little bit such that the pressing punch is moved further and a pressing punch speed of >0 is determined.

As a consequence, a match with the second speed profile upon undercutting a threshold value by the pressing punch speed can be determined. The amount of the threshold value can be identified experimentally or with the aid of computer simulations.

About ii):

This option is the option which can be implemented most easily. The period of time which corresponds to a maximum duration of the second processing phase can be identified experimentally or with the aid of computer simulations.

About iii):

As the geometric dimensions of the pre-pressing area, pressing channels and molding area as well as the volume of the dental material which is used are known the share of the molding area which has already been filled with dental material can be identified by means of the pressing punch path which has been covered. If the pressing punch path reaches a threshold value which corresponds to the volume of the used dental material in connection with the cross-sectional area of the pre-pressing area, this means that the molding area is filled with dental material. The pressing process can be canceled such that the second processing phase should finished off with the pressing process.

Further advantages, details and features of the invention may be taken from the following exemplary embodiments with reference to the drawings. Here, the same references numbers refer to the same or corresponding elements and features of different exemplary embodiments can be combined with each other.

Figure 2:
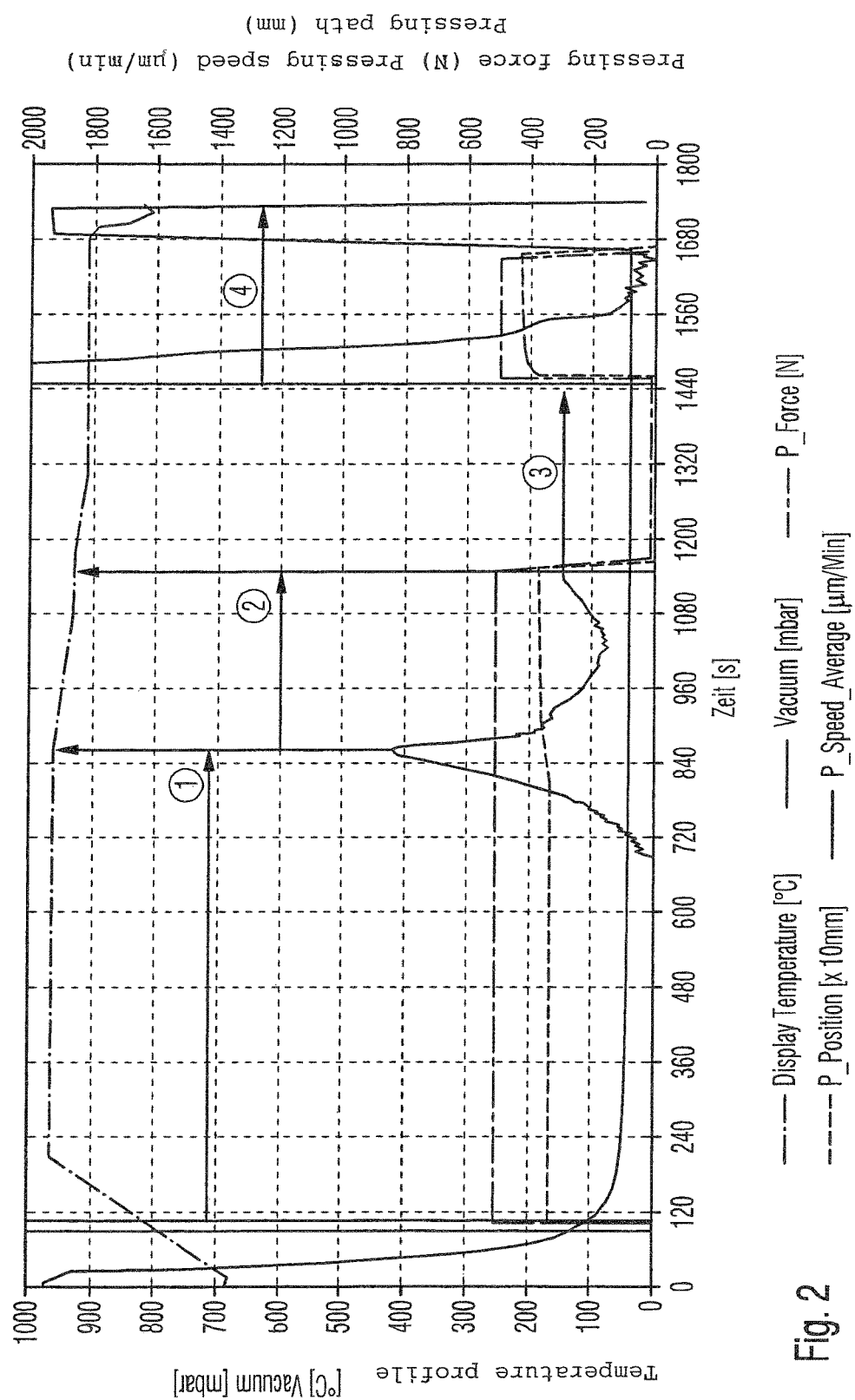

FIG. 1 shows a partial cut through an inventive pressing furnace by showing the muffle in a sectional view; and FIG. 2 shows an illustration of an inventive profile of the pressing punch speed, plotted over time.

The pressing furnace partially illustrated in FIG. 1 serves to accommodate a muffle 12 in a firing chamber 10 of the pressing furnace.

The muffle 12 is located in the firing chamber 10. It comprises cavities 14 and 16 which are intended for the formation of dental restoration parts as dead molds. The cavities 14 and 16 are connected with a pre-pressing area 22 via pressing channels 18, 20, which pre-pressing area is configured substantially cylindrically. In the pre-pressing area 22 a pressing punch 26 is mounted in a slidably moveable manner. The pressing punch 26 acts on a green product 28 made of dental material 28 which extends already partly into the pressing channels 18 and 20 in the state shown in FIG. 1.

The material of the muffle 12 consists of a hard and heat-resistant mixture of gypsum 30. Even upon pressure by the pressing force of the pressing punch 26, the shape of the cavities 14, 16 is maintained such that the dental restoration part can be produced as precisely as desired.

The cavities 14, 16 are filled at relatively large pressing force—and thus at a correspondingly high pressing punch speed. The inventive regulation ensures that dental restoration parts of high quality can be produced all the same. Here, it is particularly advantageous that if the hot dental material 28 dwells in the muffle 12 for a short period of time, the tendency towards reactions between the dental material 28 and the investment material is small.

As can be seen from FIG. 1, the firing chamber 10 is configured between a furnace hood 36 and a furnace base 38. The furnace hood 36 carries a heating element 40 known per se which surrounds the firing chamber 10 helically. The pressing punch 26 is guided in the furnace hood 36 in a pressing punch guidance 42 and is provided with a pressing punch drive 44 which also comprises a position sensor which detects the exact position—and thus also the movement of the pressing punch.

FIG. 2 shows the developments of the process parameters during one pressing cycle. The process parameters are as follows:

temperature in the firing chamber 10 of the press furnace ("Display Temperature [° C.]"), start value=stand-by temperature;

pressure in the firing chamber 10 of the press furnace ("Vacuum [mbar]"), start value=approximately 1 bar;

force acting on the pressing punch 26 ("P_Force [N]"), start value=0;

pressing punch path ("P_Position [10×mm]"), start value=0 pressing punch speed ("P-Speed_Average [mm/Min]"), start value=0.

Here, a start value is the value of a process parameter at the beginning of the pressing cycle.

The following list shows the course of events and of process parameters in tabular form in connection with the associated processing phases.

| Time [s] | Events |
|---|---|
| 0 | The pressing cycle is started, the dental material 28 is inserted into the pre-pressing area 22.<br>The heating of the firing chamber 10 to the first temperature is started and is performed at a first rate of temperature change.<br>The lowering of the pressure in the firing chamber 10 is started. |
| 100 | The first processing phase in started.<br>A constant force of approximately 250N is applied to the pressing punch 26 for pressing the dental material 28 into the molding area 14, 16, wherein the pressing punch 26 can be moved and the pressing punch speed is detected in a time-dependent manner as a speed profile.<br>Initially, this pressing punch speed continues to be = 0.<br>A pressing punch path covered by the pressing punch 26 is detected. It continues to be = 0. |
| 200 | The pressure in the firing chamber 10 which remains constant in the further course of the pressing cycle reaches a final value of approximately 70 mbar. |
| 230 | The first temperature is reached in the firing chamber 10. From that moment until the end of the first processing phase, the temperature in the firing chamber 10 is maintained unchanged at the value of the first temperature. |
| 700 | The dental material 28 starts to melt in the edge regions which are in contact with the hot molding insert 30, whereby the dental material 28 and thus the pressing punch 26 start to move. As a consequence, the pressing punch speed starts to rise.<br>The position of the pressing punch 26 is changed and the pressing force applied would decrease if it was not regulated. However, according to the invention regulation is carried out in this context. |
| 850 | The speed profile of the pressing punch 26, represented as a 2D profile of the pressing punch speed, reaches a maximum.<br>On the basis of the maximum of the pressing punch speed a match of the detected speed profile with a first speed profile which represents an impulse is determined. In the present case, the profiles are considered to be matching profiles on the basis of a similarity of the profiles. The match is determined upon reaching the maximum of the pressing punch speed.<br>The determination of the maximum of the pressing punch speed terminates the first processing phase.<br>From the point in time of the maximum at which the dental material 28 has reached the base of the molding area 14, 16 the dental material 28 starts to spread sideways in the molding area 14, 16; this decelerates the forward movement. As a consequence, the pressing punch speed decreases. On the basis of the assumption that at this point in time the dental material 28 has reached the desired temperature, a lowering of the temperature in the firing chamber 10 to the second temperature is started in order to reduce a further rise in temperature of the dental material 28.<br>The second processing phase is started.<br>However, no particular monitoring takes place in this connection. |
| 1040 | The speed profile of the pressing punch 26 reaches a minimum. From this point in time, the pressing punch speed rises. This can be an indication for the fact that a further cavity is opened up. |
| 1150 | The pressing punch speed has risen further and now it is clear that the temperature at the green product is sufficient for molding.<br>The force onto the pressing punch 26 is cut back to zero. As a consequence, the pressing punch speed also drops to zero.<br>The firing chamber 10 is cooled further towards a third temperature, at a third rate of temperature change.<br>This means that no further temperature increase is necessary.<br>The third processing phase is started. |
| 1440 | The third processing phase is terminated after expiration of a pre-determined duration of a third processing phase.<br>The waiting time provided for in this context serves to provide a sufficient temperature control and temperature homogenization across all regions in the muffle.<br>The fourth processing phase is started and involves the following changes to process parameters:<br>The constant force of approximately 250N is again applied to the pressing punch 26. The pressing punch speed rises, but drops after a short period of time again as soon as the pressing punch is in contact with the piston or green product.<br>The temperature in the firing chamber 10 is maintained unchanged at the third temperature. |
| 1670 | The pressing punch speed drops to zero which indicates that the molding area 14, 16 is completely filled with dental material.<br>The firing chamber 10 is cooled, the force acting on the pressing punch 26 is cut back to zero. As a consequence, the pressing punch speed becomes negative.<br>The third processing phase is terminated.<br>The pressing cycle is terminated. |

Below, the reference values and threshold values of the firing cycle shown in FIG. 2 are summarized.

| | |
|---|---|
| stand-by temperature | 700° C. |
| first temperature | 960° C. |
| rate of temperature change for heating the firing chamber (10) to the first temperature | 80° C./min |
| second temperature | 930° C. |
| rate of temperature change for cooling the firing chamber (10) to the second temperature | −8° C./min |
| third temperature | 910° C. |
| rate of temperature change for cooling the firing chamber (10) to the third temperature | −8° C./min |
| maximum duration of the third processing phase | 1:30 min |
| maximum duration of the fourth processing phase | 5 min |
| force acting on the pressing punch (26) | 250N |
| threshold value of the pressing punch speed in the second speed profile | 180 μm/min |

All the reference values or threshold values of the process parameters, such as the stand-by temperature, first to third temperature, rates of temperature change, force acting on the pressing punch 26, or threshold values of the pressing punch speeds, pressing punch acceleration, pressing punch path, etc., can be adjusted by an operator at the pressing furnace.

The following are ranges of parameters that are used in the process described herein:
- a stand-by temperature set to a value of 300 to 1000° C.;
- a first temperature set to a value of 700 to 1200° C.;
- a rate of temperature change for heating the firing chamber (10) to the first temperature set to a value of 50 to 110° C./min;
- a second temperature set to a value of 700 to 1100° C.;
- a rate of temperature change for cooling the firing chamber (10) to the second temperature set to a value of −1 to −15° C./min;
- a third temperature set to a value of 700 to 1100° C.;
- a rate of temperature change for cooling the firing chamber (10) to a third temperature set to a value of −5 to −15° C./min;
- a maximum duration of a fourth processing phase set to a value of 3 to 7 min.—

The process variables to be detected are detected by means of sensors, the associated analog signals are converted into digital signals and are processed by a microprocessor. In this way, e.g. the pressing punch path is measured at successive points in time, and the time series obtained in this way is used to determine the pressing punch speed and the pressing punch acceleration by means of numerical differentiation.

Instead of detecting the speed it is also possible to detect the path and to use the analog path signals detected in this way.

The invention claimed is:

1. A method of processing a dental material (28) by pressing a dental material, using a molding insert (30) that has a pre-pressing area (22) which adjoins a molding area (14, 16), wherein the pre-pressing area (22) is designed to receive the dental material (28) in the form of a green product, and using a pressing furnace with a firing chamber (10) for receiving the molding insert (30),
the method comprising the steps of:
introducing the dental material (28) into the pre-pressing area (22);
heating the firing chamber (10) in which the molding insert (30) is located, to a first temperature;
pressing the dental material (28) into the molding area (14, 16) using a pressing punch (26) by applying a force onto the pressing punch (26) during a first processing phase, wherein the pressing punch (26) is moved, and the pressing punch speed is detected as a speed profile dependent on time;
adjusting the firing chamber (10) to a second temperature during a second processing phase starting at a point in time at which the detected speed profile matches a first speed profile without reducing the force applied to the pressing punch (26); and
terminating the second processing phase by decelerating or ceasing a forward motion of the pressing punch towards pressing;
in a third processing phase the application of force onto the pressing punch (26) is suspended for a duration of the third processing phase, and
subsequently in a fourth processing phase the force is again applied to the pressing punch (26).

2. The method of claim 1, characterized by at least one of the following steps:
a match with the first speed profile is determined upon exceeding a threshold value by the pressing punch speed;
a match with the first speed profile is determined upon reaching a maximum of the pressing punch speed, wherein the first speed profile represents an impulse;
a match with the first speed profile is determined when a pressing punch acceleration exceeds a threshold value;
the pressing punch speed is detected by a position detection sensor which detects the movement of the pressing punch over time;
a detection of a path of travel is covered by the dental material and by the pressing punch by means of a path detection sensor.

3. The method of claim 1, characterized by at least one of the following steps:
the firing chamber (10) is heated to the first temperature at a first rate of temperature change;
the firing chamber (10) is heated to the first temperature starting at a stand-by temperature;
the firing chamber (10) is cooled to the second temperature at a second rate of temperature change;
the firing chamber (10) is cooled by a temperature of a maximum of 15% of the first temperature, to the second temperature;
a pressing punch path covered by the pressing punch (26) is detected;
a force in the range of 200 to 400 N which is approximately constant during the first processing phase or during the first two processing phases is applied to the pressing punch (26) in order to press the dental material (28) into the molding area (14, 16);
the application of the force onto the pressing punch (26) is started during the heating of the firing chamber (10), at the beginning of the first processing phase.

4. The method as claimed in claim 3, characterized by at least one of the following steps:
the fourth processing phase will be terminated i) after the expiration of a time period which corresponds to a maximum duration of the fourth processing phase, or ii) when a pressing punch path exceeds a threshold value;
in the third processing phase the firing chamber (10) is cooled to a third temperature starting at the second temperature;
in the fourth processing phase the firing chamber (10) is kept at a constant temperature value.

5. The method as claimed in claim 4, characterized by at least one of the following steps:
the stand-by temperature is set to a value of 300 to 1000° C.;
the first temperature is set to a value of 700 to 1200° C.;
the rate of temperature change for heating the firing chamber (10) to the first temperature is set to a value of 50 to 110° C./min;
the second temperature is set to a value of 700 to 1100° C.;
the rate of temperature change for cooling the firing chamber (10) to the second temperature is set to a value of −1 to −15° C./min;
the third temperature is set to a value of 700 to 1100° C.;
the rate of temperature change for cooling the firing chamber (10) to the third temperature is set to a value of −5 to −15° C./min;
the maximum duration of the fourth processing phase is set to a value of 3 to 7 min;
the force applied onto the pressing punch (26) is set to a value of about 250 N.

6. The method as claimed in claim 5, characterized by at least one of the following steps:
the stand-by temperature is set to a value of about 700° C.;
the first temperature is set to a value of about 960° C.;
the rate of temperature change for heating the firing chamber (10) to the first temperature is set to a value of about 80° C./min;
the second temperature is set to a value of about 930° C.;
the rate of temperature change for cooling the firing chamber (10) to the second temperature is set to a value of about −8° C./min;
the third temperature is set to a value of about 910° C.;
the rate of temperature change for cooling the firing chamber (10) to the third temperature is set to a value of about −8° C./min;
the maximum duration of the fourth processing phase is set to a value of about 5 min.

7. The method of claim 3, wherein when the firing chamber (10) is cooled, the firing chamber is cooled by a temperature of by about 5% of the first temperature, to the second temperature.

8. The method as claimed claim 1, further comprising the following step:
the second processing phase is terminated by ceasing the application of force onto the pressing punch (26).

9. The method as claimed in claim 1, wherein the second processing phase having a second speed profile is terminated with a match of the second speed profile as characterized by at least one of the following steps:
a match with a second speed profile is determined upon exceeding a threshold value by the pressing punch speed;
a match with a second speed profile is determined when a pressing punch acceleration exceeds a threshold value;
a match with a second speed profile is determined upon reaching a threshold value by the pressing punch speed.

10. The method as claimed in claim 1 wherein the molding insert comprises a muffle and wherein the step of adjusting the firing chamber comprises cooling the firing chamber.

* * * * *